US00PP11895P2

(12) United States Plant Patent
Kent

(10) Patent No.: US PP11,895 P2
(45) Date of Patent: May 29, 2001

(54) GUZMANIA PLANT NAMED 'GUZ 201'

(75) Inventor: Jeffrey C. Kent, 2074 Pleasant Heights, Vista, CA (US) 92084

(73) Assignee: Jeffrey C. Kent, Vista, CA (US)

( * ) Notice: Subject to any disclaimer, the term of this patent is extended or adjusted under 35 U.S.C. 154(b) by 0 days.

(21) Appl. No.: 09/247,342

(22) Filed: Feb. 9, 1999

(51) Int. Cl.[7] ..... A01H 5/00

(52) U.S. Cl. ..... Plt./371

(58) Field of Search ..... Plt./371

*Primary Examiner*—Bruce R. Campell
*Assistant Examiner*—Kent L. Bell
(74) *Attorney, Agent, or Firm*—James A. Lucas; Driggs, Lucas, Brubaker & Hogg Co., L.P.A.

(57) ABSTRACT

A new cultivar of Guzmania named 'GUZ 201' characterized by a plant form that is vase shaped; plant height of about 20–22 inches, and leaves measuring 21 inches in length a 1½ inches in width.

1 Drawing Sheet

BACKGROUND OF THE INVENTION

The present invention relates to a newly developed interspecific hybrid Guzmania plant resulting from a planned breeding program that I conduct on an ongoing basis. The objects of the breeding program include the crossing of selected parent plants from the numerous, compatible species within the genus, to obtain plants with novel and attractive phenotypes, coloration, and flowering forms. Other important selection factors may include ultimate plant size and shape, disease resistance, tolerance to different soil and growing conditions and vigor.

Among the objects of my program are to produce plants of the Bromeliaceae family which will be attractive to the consumer; which will develop reasonably rapidly under controlled conditions; and, retain for a long term, highly attractive and bright inflorescence; i.e., bract coloration, after being induced into the flowering stage. It is a specific object to provide a lower maintenance plant which will be a long term decorative appointment offering an exotic color splash in the home of a buyer, or to serve as a substitute for flowering plants which have a shorter flowering duration in, for example, indoor plant and flower scapes. Finally, it is an object to develop plants which may be easily and efficiently multiplied by state-of-the-art tissue culture methods while continuing the distinctive characteristics of the plants through progressive clonal generations.

This plant was a naturally occurring vegetative sport discovered as a single plant growing in a cultivated planting of Guzmania 'Minnie-Exodus' at a nursery in Vista, Calif. The parent Guzmania 'Minnie-Exodus' (unpatented) is a hybrid of *Guzmania zahnii*×*Guzmania lingulata* 'minor'. With the recognition that this sport satisfied the objects of the breeding program, the individual was isolated and set aside for further observation and testing. The resulting selection has been assigned the designation 'GUZ 201' for purposes of identification. This plant has been reproduced by division at Vista Calif., and the clonal specimens resulting therefrom have been determined to be identical to the original selection in all distinguishing characteristics. The superior attributes of this plant will be revealed in the botanical descriptions to follow.

SUMMARY OF THE INVENTION

The attributes of the plant 'GUZ 201' which distinguish it from the other clones of *Guzmania zahnii*×*Guzmania lingulata* 'minor', particularly 'GUZ 210' (U.S. Plant Pat. No. 10,069) are described as follows:

The leaves of 'GUZ 201', have marginal variegations as compared to the green margins of the leaves of 'GUZ 210' from near the base of the plant to the apex;

The abaxial side of the leaves of 'GUZ 201' is more saturated with red-purple color to the point of being nearly solid in color;

The adaxial side of the leaves is more highly colored than 'GUZ 210';

The overall dimensions of 'GUZ 201' are somewhat larger than those of 'GUZ 210' at anthesis;

'GUZ 201' grows more quickly and produces more simultaneous offsets than 'GUZ 210'. The flowers of the parent, Guzmania 'Minnie-Exodus' are identical to those of 'GUZ 201'. The major difference is in the foliage with the foliage of the parent being RHS 137-A in color adaxial and RHS 59-A abaxial. Further, the foliage of 'GUZ 201' is marginally variegated, and shows some staining.

In general 'GUZ 201' grows from offset to market stage in about 18 months. The inflorescence retains its high color for 8–10 weeks indoors. The plant retains its attractiveness long after inflorescence due to its colorful variegation.

BRIEF DESCRIPTION OF THE DRAWING

The single color photograph depicts a mature potted specimen of the plant in mid to late flowering stage. Illustrated are the mature leaves, scape bract and floral bract. The color definitions in the specification have been taken from the Colour Chart of The Royal Horticultural Society. While the colors depicted are believed to be of a high level of color fidelity, the coloration of this plant should be understood to be approximate, and somewhat variable as a function of cultural conditions and horticultural practices. For example, the bract color might slightly fade if the plant is subjected to bright light and the leaf color may vary depending on the composition and the concentration of fertilizer that may be applied to the plant.

BOTANICAL DESCRIPTION OF THE PLANT

General characteristics:

*Type.*—Monocot perennial.

*Habit.*—Medium, vigorous, spreading and dense. Production from initial transplant to anthesis when grown under coastal Southern California conditions is approximately 81 weeks.

*Hardiness.*—Tender. 'GUZ 201' is frost tender and will suffer leaf damage below 45° F.

*Size.*—About 28–30 inches in width and about 20 to 22 incheds in height, including inflorescence.

*Shape.*—Vase formed.

Leaves:

*Length.*—21 inches.

*Width.*—1½ inches. Medium size, acuminate in overall shape, acutely pointed, medium thickness, margins smooth; apetiolate ; medium to light green and smooth. Color-143-C on adaxial and abaxial sides; marginal variegations 149-D in color blending into 11-D at a apex ¼ to ⅜ inches broad; irregular interior variegation 1/32 to ⅛ inches, adaxial and abaxial sides; Lower leaves stained 63-A at base on the adaxial grading into 62-C in the middle, then back to solid 63-A at the apex; abaxial solid 63-A from the base to the apex, where the green coloration between the variegation becomes 70-A in color.

Propagation:

*Method of asexual reproduction.*—Division.

*Where reproduction took place.*—Vista, Calif.

Inflorescence: Branched.

Scape bracts: Slightly twisted below 5"×1" to 2¼"×¾", linear acute in overall shape. The margins of the lower scape bracts are 63-A abaxial and adaxial with some variegation apparent in lowest bracts; this is contrasted by 70-A color in middle of scape bract abaxial and adaxial; at apex, color blends into 143-C adaxial and abaxial in center of bract and 63-A at margins.

Floral bracts: Lanceolate in shape, 1⅛"×9/16" sharply keeled, abruptly tipped some lineation in the middle, 66-A in color abaxial and adaxial, grading into solid color towards the tips. Some tips are 63-A in color while others are 4-D.

Floral buds:

*Shape.*—Flattened oval.

*Length.*—1½" to 1¾".

*Width.*—¾" to 1¼".

*Color.*—Base is 4-D blending into 58-A at the center then back to 4-D at apex.

Flowers: Flowers without a pedical barely open at anthesis.

*Corolla.*—Cylindrical.

*Three sepals.*—1"×5/16" translucent 4-D in color (adaxial and abaxial sides).

*Three petals.*—1¼"×¼" translucent 4-D in color (adaxial and abaxial sides), joined ⅞" from base.

Fruit/seed: None produced.

Reproductive organs: Typical for the genus and the family.

*Ovaries.*—Superior, three locules ½" long by ¼" wide, 149-D in color.

*Pistils.*—1 present.

*Style.*—1½" long by ¼" wide, 149-D in color.

*Stamens.*—6 present.

*Filament.*—¾" long.

*Anthers.*—3/16" long, 7-D in color. Pollen not produced.

Disease and pest resistance: This variety has resistance to plant diseases and pests comparable to that of other variegated Guzmania cultivars.

What is claimed is:

1. A new and distinct variety of Guzmania plant named 'Guz 201' as illustrated and described herein.

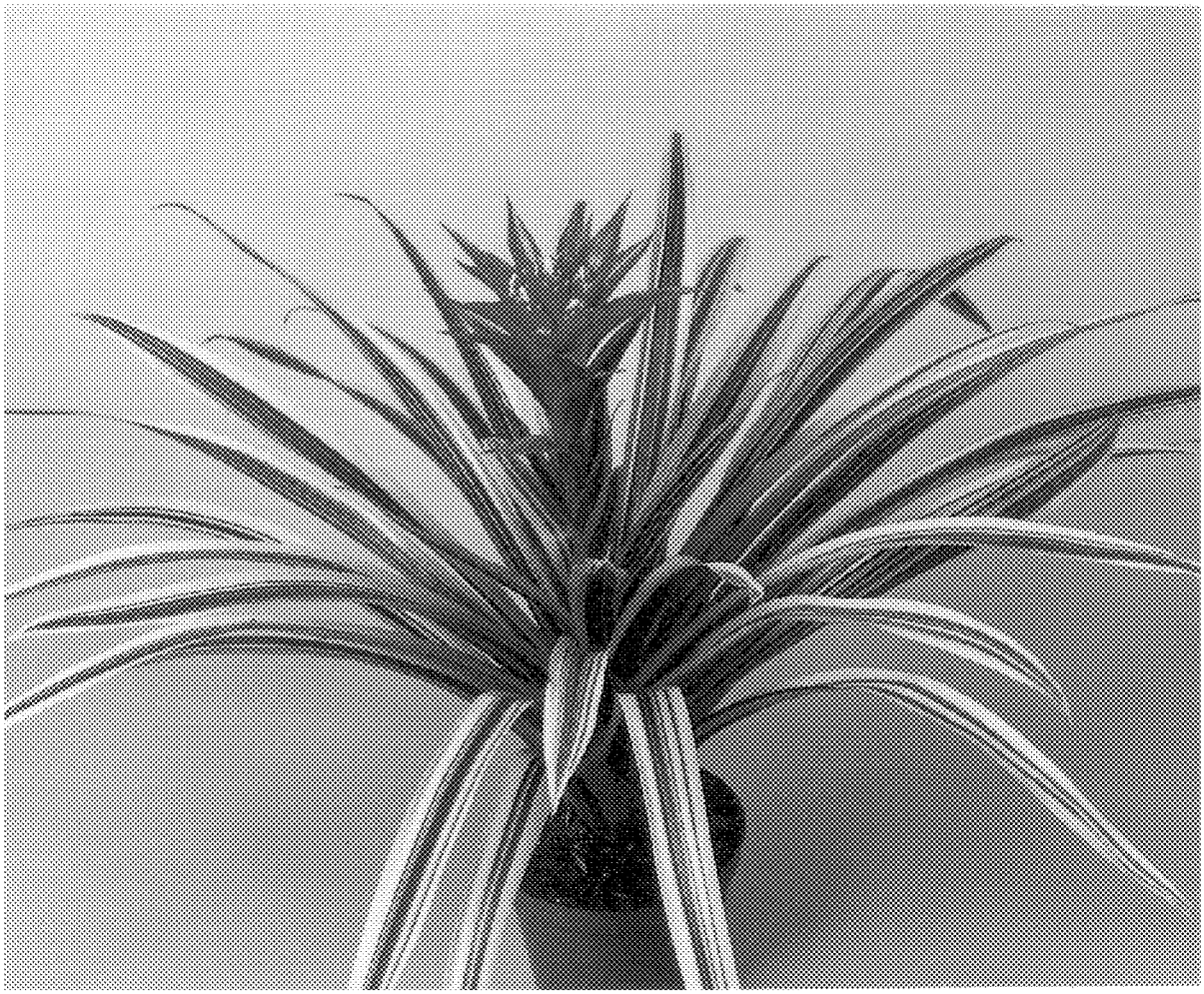

* * * * *